(12) United States Patent
Truscott

(10) Patent No.: US 6,375,681 B1
(45) Date of Patent: Apr. 23, 2002

(54) VERTEBRAL BODY REPLACEMENT

(75) Inventor: James William Truscott, Swindon (GB)

(73) Assignee: EBI, L.P., Parsippany, NJ (US)

( * ) Notice: Subject to any disclaimer, the term of this patent is extended or adjusted under 35 U.S.C. 154(b) by 0 days.

(21) Appl. No.: 09/337,779

(22) Filed: Jun. 22, 1999

(30) Foreign Application Priority Data

Jun. 23, 1998 (GB) .............................................. 9813566

(51) Int. Cl.$^7$ .................................................. A61F 2/44
(52) U.S. Cl. .................................................. 623/17.11
(58) Field of Search .......................... 623/17.11, 17.16; 606/61

(56) References Cited

U.S. PATENT DOCUMENTS

| | | | |
|---|---|---|---|
| 5,514,180 A | | 5/1996 | Heggeness et al. |
| 5,609,637 A | * | 3/1997 | Biedermann et al. ..... 623/17.16 |
| 5,702,451 A | * | 12/1997 | Biedermann et al. .. 623/170.16 |
| 5,702,453 A | * | 12/1997 | Rabbe et al. ............ 623/17.16 |
| 5,776,197 A | * | 7/1998 | Rabbe et al. ........ 623/17.16 X |
| 5,916,267 A | * | 6/1999 | Tienboon |
| 6,086,613 A | * | 7/2000 | Camino et al. |

FOREIGN PATENT DOCUMENTS

| | | |
|---|---|---|
| DE | 295 11 146 U1 | 1/1996 |
| EP | 0 266 115 A1 | 10/1987 |
| EP | 0 567 424 A1 | 4/1993 |
| EP | 0 639 351 A2 | 6/1994 |
| EP | 0 727 196 A1 | 12/1995 |
| FR | 2 774 010 | 8/1997 |
| RU | 1811822 * | 4/1993 |
| WO | WO 92/06654 | 4/1992 |
| WO | WO 96/17564 | 6/1996 |
| WO | WO 99/32055 | 7/1999 |

* cited by examiner

Primary Examiner—Jeffrey A. Smith
(74) Attorney, Agent, or Firm—Harness, Dickey & Pierce, P.L.C.

(57) ABSTRACT

A spinal prosthesis (1) comprises hollow strut (2) terminated by a pair of end caps (10, 12) which are adapted to engage respective vertebrae. Each end cap (10, 12) may have a flange (20, 22) which is closely received within and supports a respective end (6, 8) of the strut (2). Alternatively, or in addition, each end cap (10, 12) may be substantially kidney shaped and may be provided with a kidney shaped recess (16, 18) which provides access to the interior of the strut (2). Preferably, the end caps (10, 12) are provided with respective shoulders (28, 30) which are adapted to cover the ends of the strut (2) to prevent the strut damaging soft tissue during implantation. A porous titanium plasma coating may be applied to the end caps (10, 12) to enhance bone fixation and to resist anterior translation and rotation of the prosthesis (1).

19 Claims, 2 Drawing Sheets

VERTEBRAL BODY REPLACEMENT

BACKGROUND OF THE INVENTION

1. Field of the Invention

This invention relates to a spinal prosthesis for supporting or replacing all or part of one or more vertebral bodies.

2. Description of the Prior Art

The treatment of spinal fractures and tumours often requires the implantation of a prosthesis capable of substituting for the affected vertebra.

In the absence of any commercially available implants, spinal surgeons used bone cement as a crude spacer. PMMA cement has sufficient compressive strength to replace bone for the space of one vertebra. If more than two vertebrae are involved, then the cement must be reinforced with metal rods which function as compression struts.

Although PMMA cement was widely used in this application, it does have disadvantages. More specifically, it is difficult to prepare a cement bridge which is dimensionally accurately enough to restore correct spinal alignment and to install easily. Inter-operatively, soft tissues have a tendency to fold or curl over the edge of the anterior rim and enter the intervertebral space, thus causing the anterior rim to be insufficiently supported. This can lead to displacement of the cement bridge. There is also a high risk of infection with cement struts. The infection risk is increased partly because of the longevity of the surgery, and because of biological reaction with cements which contain antibiotics. Cements have been developed specifically for this type of procedure, to reduce the incidents of infection. The cement in these procedures is mixed to a dense paste and is fitted into the spine. This then cures in vivo. As it cures it generates heat, risking thermal damage to the neural pathways. A 4 to 12° C. rise in tissue temperature at the dural sac has been measured in experiments in cadavers. Although this technique is still in use today, it is confined to end stage patients.

Alternative systems have also been proposed and current commercially available instrumentation includes, among other systems, bracing devices and sophisticating jacking devices. These jacking devices all follow the same basic pattern, although to different levels of sophistication. Each uses opposite handed threaded arrangements to adjust the implant height and can be locked off once the correct height and position is achieved. They only differ in the fixing to the vertebrae, and in the degree of anatomic accuracy. These existing systems have been partially successful, but there have been reports of subsidence or anterior translation with attendant problems of hyperkyphosis and pain. The present invention has therefore been developed to address the problems associated with the existing systems of corporectomy based spinal reconstruction.

SUMMARY OF THE INVENTION

According to a first aspect of the present invention there is provided a prosthesis comprising a hollow strut terminated by a pair of end caps which are adapted to engage respective vertebrae, each end cap having a flange which is closely received within and supports a respective end of the hollow strut.

To ensure long term stability and resistance to subsidence, the end caps are preferably substantially kidney shaped so that they approximate to the anatomic shape of the hard outer cortex of the vertebral bodies of the vertebrae.

According to a second aspect of the present invention, there is provided a prosthesis comprising a strut having a pair of end caps which are adapted to engage respective vertebrae, each end cap being substantially kidney shaped in a plane substantially perpendicular to the longitudinal axis of the strut.

Preferably the strut is substantially kidney shaped in cross-section, so that the prosthesis as a whole has a posterior concavity which, when implanted, accommodates the spinal cord.

Any spinal prosthesis is subject to compression, torsion and cyclic fatigue loads. By far the largest component of force is a cyclic compressive component which must be transmitted at the interface between the end plate of the adjacent vertebral body and the prosthesis. The anatomy of the vertebral body end plate is well documented and is not discussed in detail here. Put simply, the end plate is approximately kidney shaped and has a soft cancellous centre and a hard outer cortex of bone capable of withstanding compressive loading. Therefore, in a preferred embodiment of the invention, the end caps have a large cutout which corresponds in shape to the outer rim, and allows contact between bone graft packed inside the implant and the vertebral body end plate, or in cases where the device has been packed with cement, to allow for any excess to escape and be removed.

According to a third aspect of the present invention there is provided a prosthesis comprising a strut having a pair of end caps which each have an end wall which is adapted to engage a respective vertebra, the periphery of each end wall extending further from the strut than the remainder of the end wall.

Preferably, the end caps are a press fit into the hollow strut. Preferably, the leading edge of each flange is chamfered, which assists alignment of the end cap with the hollow strut and facilitates assembly.

Preferably, the strut comprises a tube. The tube may be seam welded or extruded.

Preferably, the tube is made of titanium and may be heat treated. Preferably, the tube has a 0.9 mm thick wall.

The strut may be provided with a plurality of through holes. Preferably, the hole pattern is configured to enable trimming to length to suit individual patient need, such as to allow for a degree of lordoeses and kyphoses.

Preferably, in a region away from the periphery, the end wall is provided with a kidney shaped recess.

Preferably, the recess comprises a through hole which provides access to the interior of the strut.

Preferably, each end cap is provided with a shoulder which is adapted to cover the end of the strut and to prevent the end of the strut damaging the surrounding soft tissue.

Preferably, the prosthesis is stabilized by rods and bone screws. For example, 5 mm diameter transvertebral rods and 6.5 mm diameter bone screws may be used. These screws and rods are preferably based on a top loading collet locking system such as the Webb-Morley system. The screws and rods are preferably used anteriorly to bridge the prosthesis and may also be used posteriorly to further strengthen the total assembly.

Preferably a porous titanium plasma coating is applied to the end caps to enhance bone fixation and to resist anterior translation and rotation of the prosthesis by biting into the subcondral bone. When the prosthesis is implanted and under a compression load, there will be intimate contact between the porous coating and the bone. This helps enhance primary stability and encourages osseointegration.

According to a fourth aspect of the present invention there is provided a prosthesis comprising a strut, the ends of the strut being adapted to engage respective vertebrae, the strut comprising a tube.

Preferably each end of the strut is provided with an end cap which is adapted to engage a respective vertebra.

The wall of the tube may be perforated, but otherwise is preferably continuous to enhance its strength. The tube may, for example, be seam welded or extruded.

It is well known that the human spine is curved along its length substantially in a median plane of the body. Consequently, although the spine looks quite straight when viewed from the front or from behind, when viewed from the side there are a series of curvatures alternating in direction. The cervical and lumbar curves are forwarded convexities and are known as lordoses. The thoracic and sacral curves are forward concavities and are known as kyphoses. As a result of this curvature in the spine, in the adult the vertebral bodies are somewhat wedge-shaped to conform to the shape of the curves. The curvature of the spine in the side to side direction of the human body also occurs and is known as scoliosis. Such curvature can be created locally in the spine by a burst fracture resulting from a side impact.

If a vertebral body replacement prosthesis must be inserted in a region of the spine which is curved, or if it is required to treat such curvature by adjusting the shape of the prosthesis, it is necessary to offset the bone engaging surfaces at the ends of the prosthesis so that they are no longer perpendicular to a plane extending parallel to the longitudinal axis of the prosthesis. The offsetting of the bone engaging surfaces of a prosthesis, which comprises a central strut and a pair of end caps, can be achieved by trimming one or both ends of the strut, so that one or both end caps are offset in the respective end(s) of the strut. A disadvantage of this approach is that offset end caps are less securely connected to the strut.

According to a fifth aspect of the present invention there is provided a vertebral body replacement prosthesis comprising a strut terminated at one end by an end cap which is adapted to engage a vertebra, the end cap having an inwardly directed end which is adapted directed towards the strut and an outwardly directed end, which, in use, is directed towards the vertebra, the outwardly directed end defining a vertebra engaging surface which is offset from a plane perpendicular to the longitudinal axis of the strut.

Preferably a further end cap is provided at the other end of the strut. This end cap may also have a vertebra engaging surface which is offset from a plane perpendicular to the longitudinal axis of the strut.

Preferably the or each end cap is substantially wedge-shaped.

Preferably, in use, the vertebra engaging surface of the or each end cap is offset relative to a plane perpendicular to the coronal plane of a patient in which the prosthesis is implanted. In addition, or instead, in use, the vertebra engaging surface of the or each end cap may be offset relative to a plane perpendicular to the median plane of a patient in which the prosthesis is implanted.

Preferably, the respective offsets are between −10° to +10°. Most preferably, the offsets are between −5° to +5°.

It will be appreciated that the various features of the invention which are described in relation to a particular aspect of the invention may also be applicable to the other aspects of the invention.

BRIEF DESCRIPTION OF THE DRAWINGS

For a better understanding of the present invention and to show how it may be carried into effect, references will now be made, by way of example, to the accompanying drawings, in which.

DETAILED DESCRIPTION OF THE PREFERRED EMBODIMENT

Figure 1:
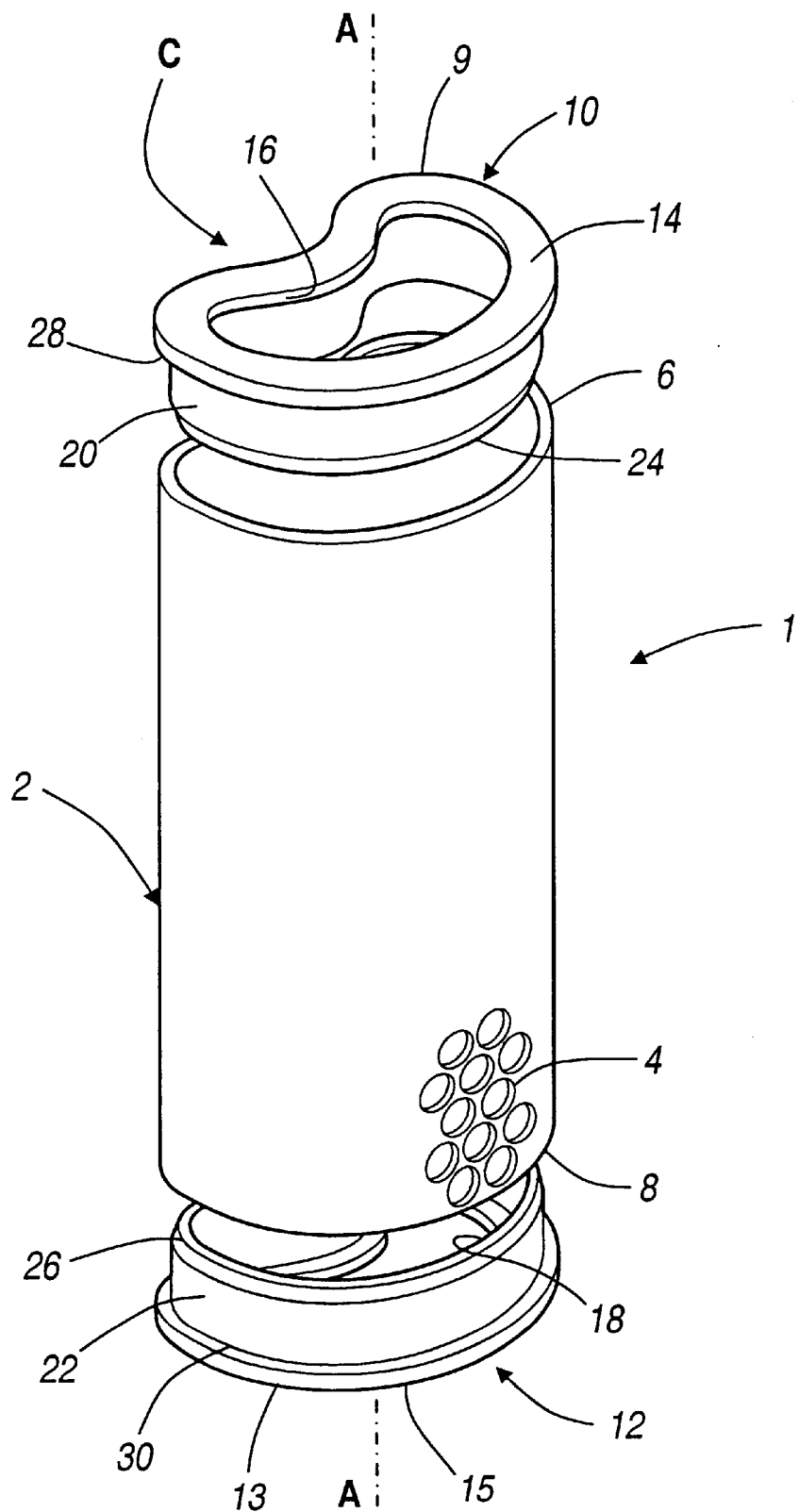
FIG. 1 is a perspective view of a prosthesis in accordance with the present invention.

FIG. 1 shows a prosthesis for use in the treatment of spinal tumours and fractures. The prosthesis 1 comprises a strut 2 formed from a heat treated titanium tube in which are formed a plurality of perforations 4. The ends 6, 8 of the strut 2 are terminated by respective end caps 10, 12 which are push fit into the ends 6, 8.

The strut 2 and end caps 10, 12 have a substantially kidney shaped cross-section and the internal diameter of the strut is sized such that the end caps 10, 12 are closely received within the ends 6, 8 of the strut 2.

Each end cap 10, 12 comprises an end wall 9, 13 having a bone engaging surface 14, 15 which is disposed in a plane substantially perpendicular to the longitudinal axis AA of the strut 2. A kidney shaped central opening 16, 18 is formed in each end wall 9, 13 and limits the bone engaging surface 14, 15 to the periphery of the end wall 9, 13 of the respective end cap 10, 12. A continuous flange 20, 22 projects at right angles from the end wall 9, 13 and forms the main body of each end cap 10, 12. The free end 24, 26 of each flange 20, 22 is chamfered to ease insertion into the strut 2.

The end wall 9, 13 of each end cap 10, 12 extends radially outwardly beyond the respective flanges 20, 22 to form shoulders 28, 30.

In a vertebral body replacement operation, the damaged or tumorous vertebral body (not shown) is cut away and the strut 2 is trimmed, so that the prosthesis as a whole will be of the correct length to replace the excised vertebral body. The end caps 10, 12 are then pushed into the open ends of the strut 2 until the respective shoulder 28, 30 abuts the respective end 6, 8 of the strut 2. As will be appreciated, the shoulders 28, 30 cover the otherwise exposed ends 6, 8 of the strut 2, which may be rough or jagged, following the trimming operation.

Following assembly, the prosthesis is inserted into the space left by the excised vertebral body, such that the spinal cord is accommodated by the posterior concavity C generated by the kidney shaping of the end caps 10, 12 and the strut 2 and such that the bone engaging surfaces 14 engage the end plates of the adjacent vertebral bodies. As discussed above, the vertebral body end plates are approximately kidney shaped and have a soft cancellous centre and hard outer cortex of bone capable of withstanding compression loading. In the implanted condition, the kidney shaped bone engaging surfaces 14 of the end caps 10, 12 are aligned with the hard outer cortex of bone of the vertebral body end plates and the openings 16, 18 are aligned with the soft cancellous centre of the end plates, so that the compressive loading on the spine is carried directly from the hardest part of the end plates into the bone engaging surfaces 14, 15 of the respective end cap 10, 12.

Prior to insertion of the prosthesis, bone graft or bone cement may be packed inside the interior of the strut 2 through the openings 16, 18 in the end caps 10, 12. If the interior of the strut 2 and end caps 10, 12 is completely filled with bone cement, the adjacent vertebral bodies will impinge directly on the bone cement which fills the openings 16, 18 so that there will be direct contact not only between the bone engaging surfaces 14 and the hard outer cortex of the end plate but also between the bone cement and the soft cancellous centre of the end plates. Any excess bone cement will be squeezed to the outside of the prosthesis and can be removed, so that once the bone cement has set, the prosthesis is an exact fit between the adjacent vertebral bodies and is therefore resistant to dislocation. Furthermore, as the load is transferred into the strongest parts of the adjacent vertebral bodies, post-operatively, the patient's spine will be able to withstand substantially the same compressive loads that it could withstand pre trauma or disease.

In order to improve the stability of the prosthesis, the bone engaging surfaces 14, 15 are provided with a porous titanium plasma coating which roughens the bone engaging surfaces 14, 15 and causes them to bite into the subcondral bone. The titanium porous coating acts as a host media for bony ingrowth, so long term fixation is also improved.

Figure 2B:
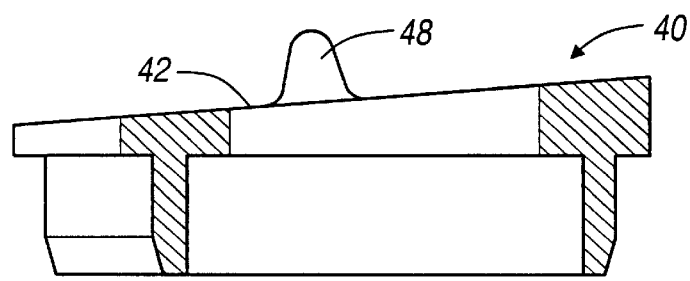
FIG. 2B is a cross-section through the end cap of FIG. 2A when viewed in the median plane of a patient.
Figure 2A:
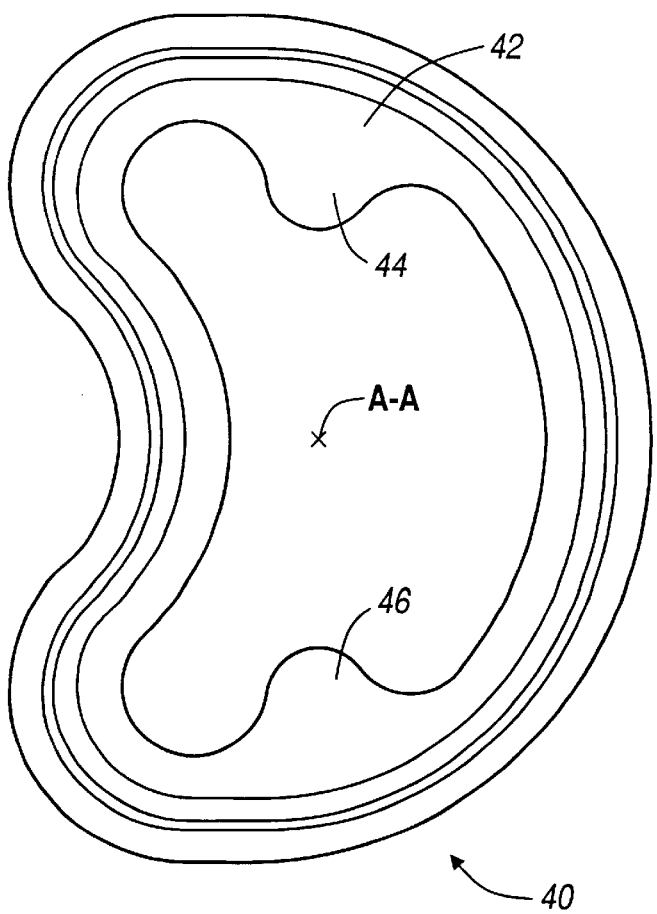
FIG. 2A is a plane view of a second embodiment of end cap with an offset bone engaging surface.
Figure 2C:
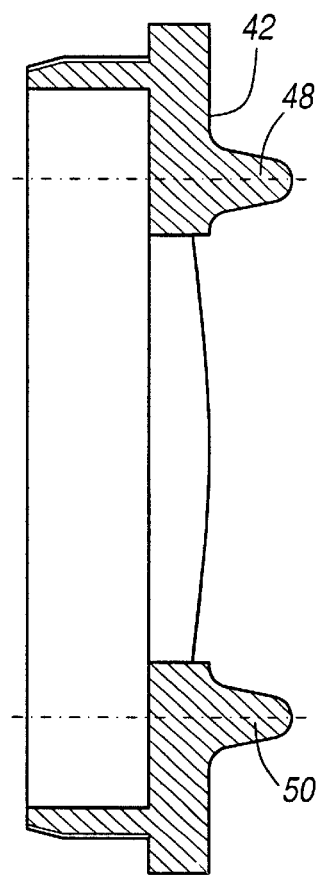
FIG. 2C is a cross-section through the end cap of FIG. 2A and 2B when viewed in the coronal plane of a patient.

FIGS. 2A, 2B and 2C illustrate a further embodiment of an end cap 40, for use with the strut 2, in which the bone engaging surface 42 is offset from a plane perpendicular to the longitudinal axis A—A of the strut 2. A further modification of this end cap 40 is the provision of extensions 44, 46 on the bone engaging surface 42 which support respective projecting bone engaging pins 48, 50. These pins 48, 50 engage in the adjacent vertebral body and further improve the stability of the prosthesis.

FIG. 2B is a cross-section through the end cap 40 along the median plane of a patient in which the prosthesis is implanted. As discussed previously, the normal human spine is curved in the median plane by a series of lordoses and kyphoses. As a result, in the adult, the vertebral bodies are somewhat wedged-shaped. Thus, in accordance with this embodiment of the invention, the bone engaging surface 42 is offset from a plane perpendicular to the longitudinal axis A—A of the strut 2. If a pair of such end caps are assembled to a strut 2, the prosthesis as a whole is generally wedge-shaped and mimics the anatomical shape of the vertebral body which it replaces. It is contemplated that inter-operatively, a surgeon will be provided with a series of replacement end caps having various different offsets relative to the median and/or coronal plane, so that he can choose an appropriate end cap to reproduce the natural anatomical shape of the spine of the patient on whom he or she is operating. If the surgeon wishes to apply a degree of correction in respect of lordoses, kyphoses or scoliosis, he or she can choose a prosthesis having a slightly lesser or greater offset that the vertebral body which is being replaced.

In a preferred embodiment, the degree of offset is approximately 2-½ to 5° in the median plane.

It will be appreciated that a single prosthesis in accordance with the present invention may be used to replace or support all or part of more than one vertebral body.

While particular embodiments of the present invention have been shown and described, it will be appreciated by those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation.

The actual scope of the invention is intended to be defined in the following claims when viewed in their proper perspective based on the prior art.

What is claimed is:

1. A prosthesis comprising:
    a hollow strut having a first hollow end and a second hollow end with a longitudinal axis that extends from the first hollow end to the second hollow end; and
    a pair of end caps which are adapted to be push fit into the first and second hollow ends with each end cap including a flange which is closely received within and supports the first and second ends of the hollow strut, each end cap further including a pair of extensions lying along an axis defined by a coronal plane and being substantially perpendicular to the longitudinal axis, each extension having a distal tip that extends along the axis defined by the coronal plane and into a central opening in each end cap, each extension having a bone engaging pin extending substantially parallel to the longitudinal axis from the distal tip, wherein the bone engaging pins engage adjacent vertebral bodies to improve stability of the prosthesis.

2. The prosthesis as defined in claim 1, in which the leading edge of each flange is chamfered.

3. The prosthesis as defined in claim 1, in which the end caps are substantially kidney shaped.

4. The prosthesis as defined in claim 1, in which each end cap is provided with a shoulder which is adapted to cover the end of the strut.

5. The prosthesis as defined in claim 1, in which a porous titanium plasma coating is applied to the end caps.

6. The prosthesis as defined in claim 1, in which the strut comprises a tube.

7. The prosthesis as defined in claim 6 in which the tube is made from titanium.

8. The prosthesis as defined in claim 7, in which the tube is heat treated.

9. The prosthesis as defined in claim 7, in which the tube is seam welded.

10. The prosthesis as defined in claim 1, in which the strut is provided with a plurality of through holes.

11. The prosthesis as defined in claim 10, in which the through holes are aligned in rows substantially perpendicular to the longitudinal axis of the strut.

12. A prosthesis comprising:
    a hollow strut having a first hollow end an a second hollow end with a longitudinal axis extending from the first hollow end and the second hollow end, said strut having a substantially kidney shaped cross-section; and
    a pair of end caps which are substantially kidney shaped in a plane substantially perpendicular to the longitudinal axis of the strut, with each having a central substantially kidney shaped opening passing therethrough, each end cap further including a pair of extensions lying along an axis defined by a coronal plane and being substantially perpendicular to the longitudinal axis, each extension having a distal tip that extends along the axis defined by the coronal plane and into the kidney shaped opening in each end cap, each extension having a bone engaging pin extending substantially parallel to the longitudinal axis from the distal tip, wherein the bone engaging pins engage adjacent vertebral bodies to improve stability of the prosthesis.

13. A prosthesis comprising:
    a hollow strut having a first hollow end and a second hollow end with a longitudinal axis that extends from the first hollow end to the second hollow end; and a pair of end caps with each having an end wall which is adapted to engage a respective vertebra, a periphery of each end wall extending further from the strut than a remainder of the end wall, each end wall defining a central opening passing through each end cap and having a pair of extensions lying along an axis defined by a coronal plane and being substantially perpendicular to the longitudinal axis, each extension having a distal tip that extends along the axis defined by the coronal plane and into the central opening, each extension having a bone engaging pin extending substantially parallel to the longitudinal axis from the distal tip, wherein the bone engaging pins engage adjacent vertebral bodies to improve stability of the prosthesis.

14. The prosthesis as defined in claim 13 wherein the central opening is kidney shaped.

15. A vertebral body replacement prosthesis comprising:

a strut terminated at one end by an end cap which is adapted to engage a vertebra, the end cap having an inwardly directed end which is directed towards the strut and an outwardly directed end which, in use, is directed toward the vertebra, the outwardly directed end defining a vertebra engaging surface which is offset from a plane extending perpendicular to the longitudinal axis of the strut, the outwardly directed end defined by a pair of extensions lying along an axis defined by a coronal plane and being substantially perpendicular to the longitudinal axis, each extension having a distal tip that extends along the axis defined by the coronal plane and into a central opening of the end cap with each extension having a bone engaging pin that extends substantially parallel with the longitudinal axis from the distal tip, wherein the bone engaging pins engage adjacent vertebral bodies to improve stability of the prosthesis.

16. The prosthesis as defined in claim 15, in which a further end cap is provided at the other end of the strut.

17. The prosthesis as defined in claim 15, in which the end cap is substantially wedge-shaped.

18. The prosthesis as defined in claim 15, in which the offset is between −10 to +10°.

19. The prosthesis as defined in claim 18, in which the offset is between −5 to +5°.

* * * * *

UNITED STATES PATENT AND TRADEMARK OFFICE
CERTIFICATE OF CORRECTION

PATENT NO. : 6,375,681 B1
DATED : April 23, 2002
INVENTOR(S) : James William Truscott It is certified that error appears in the above-identified patent and that said Letters Patent is hereby corrected as shown below:

Title page,
Item [56], FOREIGN PATENT DOCUEMENTS, "EP 266 115" should be -- EP 268 115 --.

Column 1,
Line 22, "accurately" should be -- accurate --.

Column 4,
Line 10, "FIG." should be -- FIGS. --.

Column 5,
Line 53, "that" should be -- than --.

Column 6,
Line 46, "an" should be -- and --.

Signed and Sealed this

Third Day of December, 2002

JAMES E. ROGAN
*Director of the United States Patent and Trademark Office*